US00PP20393P2

(12) United States Plant Patent
Pieters

(10) Patent No.: US PP20,393 P2
(45) Date of Patent: Oct. 6, 2009

(54) ***CHRYSANTHEMUM* PLANT NAMED 'PPP OLW 07'**

(50) Latin Name: *Chrysanthemum morifolium*
Varietal Denomination: PPP OLW 07

(75) Inventor: Dirk Pieters, Oostnieuwkerke (BE)

(73) Assignee: Paraty BVBA, Oostnieuwkerke (BE)

( * ) Notice: Subject to any disclaimer, the term of this patent is extended or adjusted under 35 U.S.C. 154(b) by 0 days.

(21) Appl. No.: 12/218,918

(22) Filed: Jul. 18, 2008

(51) Int. Cl.
*A01H 5/00* (2006.01)

(52) U.S. Cl. ..... Plt./293
(58) Field of Classification Search ..... Plt./293, Plt./287
See application file for complete search history.

*Primary Examiner*—June Hwu
(74) *Attorney, Agent, or Firm*—Mark P. Bourgeois

(57) ABSTRACT

A new and distinct *Chrysanthemum* plant cultivar is disclosed, characterized by large decorative type inflorescences, consistent flowering response to short days, blooming consistently after 49 days of short day length, red inflorescences with a darker red center, free branching habit, and a consistent natural season flowering habit during the last week of September.

1 Drawing Sheet

Latin name of the genus and species: *Chrysanthemum morifolium.*

Variety denomination: 'PPP OLW 07'.

BACKGROUND OF THE INVENTION

The new cultivar 'PPP OLW 07' is a product of a cross between the male parent 'GEDI TWO CAM' (U.S. Plant Patent No. 14,472) and the female parent 'GEDI ONE IBE' (U.S. Plant Pat. No. 13,873). The new cultivar was discovered and selected by Dirk Pieters in September of 2001 in Oostnieuwkerke, Belgium.

Asexual reproduction of the new cultivar 'PPP OLW 07' by terminal cuttings was performed in Oostnieuwkerke, Belgium and Oxnard, Calif., and has shown that the unique features of this new cultivar are stable and reproduced true to type on successive generations.

SUMMARY OF THE INVENTION

The cultivar 'PPP OLW 07' has not been observed under all possible environmental conditions. The phenotype may vary somewhat with variations in environment such as temperature, daylength, and light intensity, without, however, any variance in genotype.

The following traits have been repeatedly observed and are determined to be the unique characteristics of 'PPP OLW 07.' These characteristics in combination distinguish 'PPP OLW 07' as a new and distinct *Chrysanthemum* cultivar:

1. Large, red decorative type inflorescences with a darker red center;
2. Free branching habit;
3. Consistent natural season flowering habit during the last week of September; and
4. Consistent flowering response to short days, blooming consistently after 49 days of short day length.

Plants of the new cultivar 'PPP OLW 07' are similar to plants of the male parent variety, 'GEDI TWO CAM' in most horticultural characteristics, however plants of the new cultivar 'PPP OLW 07' are shorter. Also, the ray florets of the new cultivar 'PPP OLW 07' are a different color. Additionally, the new cultivar 'PPP OLW 07' has longer inflorescence longevity. Finally, 'PPP OLW 07' naturally blooms three to four weeks later than the male parent 'GEDI TWO CAM.'

Plants of the new cultivar 'PPP OLW 07' are similar to plants of the female parent variety, 'GEDI ONE IBE' in most horticultural characteristics, however plants of the new cultivar 'PPP OLW 07' are shorter. Also, the new cultivar 'PPP OLW 07' has a smaller inflorescence diameter and longer inflorescence longevity. Additionally, 'PPP OLW 07' has different color ray florets than the female parent. Finally, 'PPP OLW 07' naturally blooms three to four weeks later than the female parent 'GEDI ONE IBE.'

In comparison to the commercially available variety 'GEDI TWO ARE' (U.S. Plant Pat. No. 14,473), 'PPP OLW 07' has a wider plant spread but is shorter in height. Additionally, the new variety 'PPP OLW 07' has darker green foliage and smaller leaves. Further, the new variety 'PPP OLW 07' blooms one week later and has darker red ray florets. Finally, the new variety 'PPP OLW 07' has longer inflorescence longevity.

BRIEF DESCRIPTION OF THE PHOTOGRAPH

The accompanying photograph illustrates in full color a typical plant of 'PPP OLW 07' grown in a 2 gallon container. One cutting was used in the pot, planted mid May and grown under outdoor field conditions. The colors are as nearly true as is reasonably possible in a color representation of this type.

DETAILED BOTANICAL DESCRIPTION

In the following description, color references are made to The Royal Horticultural Society Colour Chart except where general terms of ordinary dictionary significance are used. The following observations and measurements describe 'PPP OLW 07' plants grown in Oxnard, Ventura County, Calif., during the months of May through October 2006. The growing temperature ranged from 12° C. to 15° C. at night to 12° C. to 20° C. during the day. Measurements and numerical values represent averages of typical flowering types.

Botanical classification: *Chrysanthemum morifolium* 'PPP OLW 07.'
Commercial classification: Garden-type *Chrysanthemum.*

PROPAGATION

Time to rooting: 7 to 14 days at approximately 21° C.
Root description: Fine, fibrous.

PLANT

Growth habit: Mounding herbaceous perennial.
Height: Approximately 18 cm.
Plant spread: Approximately 33 cm.
Growth rate: Moderate.
Branching characteristics: Free Branching.
Length of lateral branches: Approximately 12 cm.
Number of leaves per lateral branch: Approximately 15.
Age of plant described: Approximately 141 days.

FOLIAGE

Leaf:
*Arrangement.*—Alternate single.
*Average length.*—Approximately 3.9 cm.
*Average width.*—Approximately 2.1 cm.
*Shape of blade.*—Ovate.
*Apex.*—Acuminate.
*Base.*—Attenuate.
*Attachment.*—Stalked.
*Margin.*—Serrate.
*Texture of top surface.*—Lightly pubescent.
*Texture of bottom surface.*—Lightly pubescent.
*Leaf internode length.*—Approximately 0.9 cm.
*Color.*—Young foliage upper side: Near Green 139A. Young foliage under side: Near Yellow-Green 147B. Mature foliage upper side: Near Green 139A. Mature foliage under side: Near Green 137A.
*Venation.*—Type: Palmately net. Venation color upper side: Near Green 137D. Venation color under side: Near Green 138B.
Petiole:
*Average length.*—Approximately 1.2 cm.
*Color.*—Near Green 138B.
*Diameter.*—Approximately 0.2 cm.

BLOOM

Inflorescence:
*Flowering habit.*—Induced by darkness period greater than 13.5 hours, approximately 49 days of appropriate day length required to induce and develop blooms.
*Inflorescence form.*—Decorative.
*Natural flowering season.*—Approximately the last week in September.
*Number of inflorescences per lateral branch.*—Approximately 11.
*Inflorescence diameter.*—Approximately 4.7 cm.
*Inflorescence depth.*—Approximately 2 cm.
*Inflorescence longevity on plant.*—Approximately 28 to 34 days.
*Persistence.*—Persistent.
Ray florets:
*Appearance.*—Matte.
*Texture.*—Smooth.
*Average number of ray florets per inflorescence.*—200.
*Shape.*—Oblanceolate.
*Aspect.*—Flat.
*Margin.*—Entire.
*Apex.*—Obtuse.
*Length.*—Approximately 2.2 cm.
*Width.*—Approximately 0.4 cm.
*Color.*—Upper surface at first opening: Near Greyed-Purple 185A. Upper surface at maturity: Near Greyed-Red 181A. Upper surface at fading: Near Greyed-Red 180A. Under surface at first opening: Near Greyed-Purple 185A. Under surface at maturity: Near Greyed-Red 181B. Under surface at fading: Near Greyed-Red 182D. Center ray florets: Near Greyed-Purple 185A throughout maturity.
Disc florets:
*Appearance.*—Shiny.
*Texture.*—Smooth.
*Average number of florets per disc.*—Approximately 3.
*Shape.*—Cylindric.
*Apex.*—Obtuse.
*Average length.*—Approximately 0.3 cm.
*Average width.*—Approximately 0.1 cm.
*Color.*—At first opening: Near Yellow-Green 154D. At maturity: Near Yellow 13A. At fading: Near Yellow 13C.
Peduncle:
*Length.*—At terminal end (shortest): Approximately 4.9 cm. At lateral end (longest): Approximately 7.5 cm.
*Angle to stem.*—Acute.
*Strength.*—Moderate.
*Color.*—Near Yellow-Green 148B.
*Habit.*—Upright.
*Diameter.*—Approximately 0.1 cm.
*Surface texture.*—Lightly pubescent.
Inflorescence bud:
*Length.*—Approximately 1.5 cm.
*Diameter.*—Approximately 1 cm.
*Form.*—Globular.
*Color.*—Near Greyed-Purple 185A.
Involucral bracts (phyllaries):
*Appearance.*—Matte.
*Texture.*—Lightly pubescent.
*Number.*—Approximately 28.
*Shape.*—Ovate.
*Margin.*—Entire.
*Apex.*—Acute.
*Length*—Approximately 0.8 cm.
*Width.*—Approximately 0.4 cm.
*Color.*—Upper side: Near Green 137A. Under side: Near Green 137B.

REPRODUCTIVE ORGANS

Ray florets:
*Number of pistils per floret.*—1.
*Stigma shape.*—2 branched.
*Stigma color.*—Near Yellow 9A.
*Style color.*—Near Yellow-Green 154D.
*Style length.*—Approximately 0.3 cm.
*Stamens.*—Absent.
Disc florets:
*Number of pistils per floret.*—1.
*Stigma shape.*—Cylindric.
*Stigma color.*—Near Yellow 13A.
*Style length.*—Approximately 1 cm.

*Style color.*—Near Green-Yellow 1D.
*Number of stamens per floret.*—Approximately 5.
*Anther shape.*—Tubular.
*Anther color.*—Near Yellow 13A.
*Pollen color.*—No pollen detected.

OTHER CHARACTERISTICS

Disease resistance: Neither resistance nor susceptibility to diseases or pests has been observed in this variety.

Drought tolerance/cold tolerance: Flowering plants are hardy to low temperatures about −2° C. Non-flowering plants are hardy in the approximate range of 3° C. to −6° C., depending upon duration of cold and amount of moisture in the soil. With adequate water plants are hardy to a high temperature of 45° C.

Fruit/seed production: Commercially, this plant is not used or observed in a stage where seeds would be produced. Therefore, seed production has not been observed.

What is claimed is:

1. A new and distinct cultivar of *Chrysanthemum* plant named 'PPP OLW 07' as herein illustrated and described.

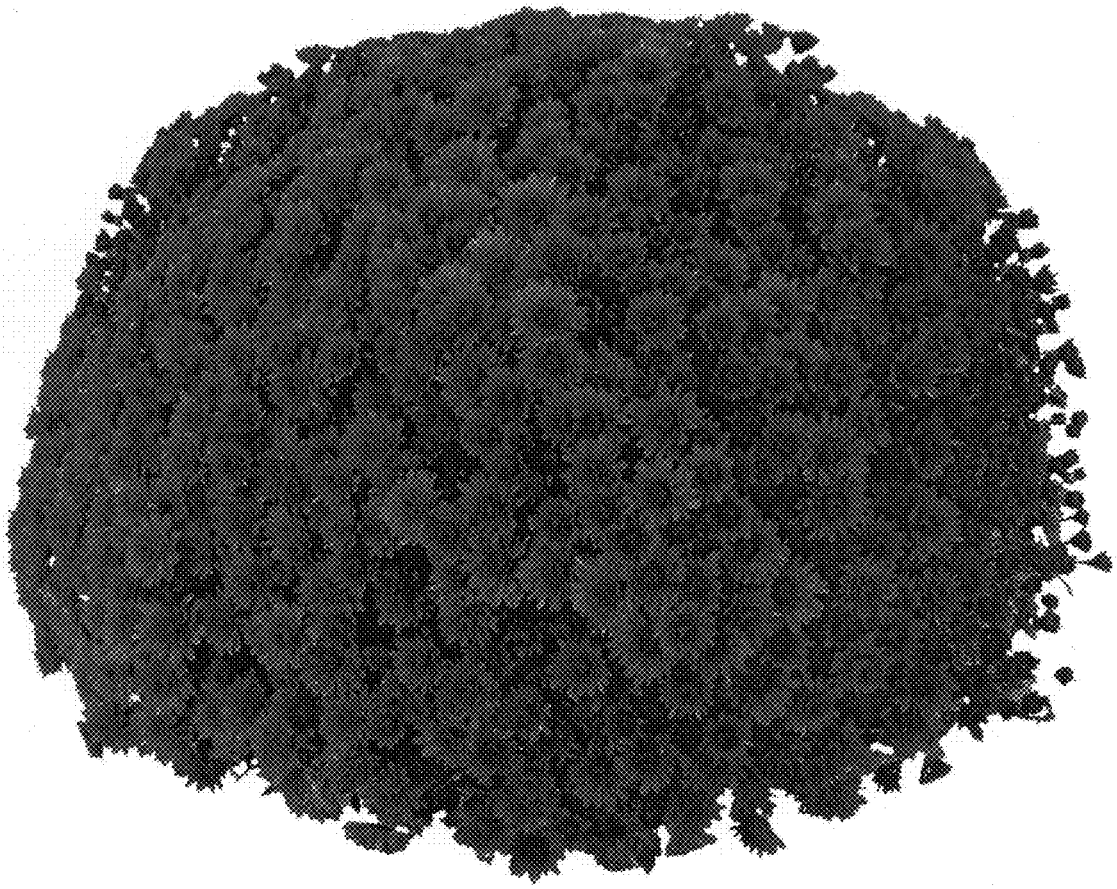

* * * * *